United States Patent
Monteleone et al.

(10) Patent No.: US 10,006,029 B2
(45) Date of Patent: Jun. 26, 2018

(54) METHODS OF TREATING COLORECTAL CANCER

(71) Applicant: Nogra Pharma Limited, Dublin (IE)

(72) Inventors: Giovanni Monteleone, Rome (IT); Salvatore Bellinvia, Pordenone (IT); Francesca Viti, Sesto San Giovanni (IT)

(73) Assignee: Nogra Pharma Limited, Dublin (IE)

( * ) Notice: Subject to any disclaimer, the term of this patent is extended or adjusted under 35 U.S.C. 154(b) by 143 days.

(21) Appl. No.: 14/211,471

(22) Filed: Mar. 14, 2014

(65) Prior Publication Data

US 2014/0271860 A1    Sep. 18, 2014

Related U.S. Application Data

(60) Provisional application No. 61/790,488, filed on Mar. 15, 2013.

(51) Int. Cl.
*A61P 35/00* (2006.01)
*C12N 15/113* (2010.01)

(52) U.S. Cl.
CPC .......... *C12N 15/1135* (2013.01); *A61P 35/00* (2018.01); *C12N 2310/11* (2013.01); *C12N 2310/315* (2013.01)

(58) Field of Classification Search
CPC .................................................. C12N 15/1135
See application file for complete search history.

(56) References Cited

U.S. PATENT DOCUMENTS

| | | | |
|---|---|---|---|
| 6,159,697 A * | 12/2000 | Monia et al. | 435/6.14 |
| 7,700,572 B2 | 4/2010 | Steinbrecher et al. | |
| 7,700,757 B2 | 4/2010 | Monteleone | |
| 7,807,818 B2 | 10/2010 | Monteleone | |
| 8,106,182 B2 | 1/2012 | Monteleone | |
| 8,648,186 B2 | 2/2014 | Monteleone | |
| 8,907,078 B2 | 12/2014 | Monteleone | |
| 8,912,154 B2 | 12/2014 | Baroni et al. | |
| 9,006,418 B2 | 4/2015 | Monteleone | |
| 9,096,854 B1 | 8/2015 | Monteleone | |
| 9,279,126 B2 | 3/2016 | Monteleone | |
| 9,314,434 B2 | 4/2016 | Baroni et al. | |
| 9,382,541 B2 | 7/2016 | Monteleone | |
| 9,499,819 B2 | 11/2016 | Baroni et al. | |
| 9,518,264 B2 | 12/2016 | Monteleone | |
| 9,605,264 B2 | 3/2017 | Monteleone | |
| 2005/0119203 A1 | 6/2005 | Steinbrecher et al. | |
| 2007/0042985 A1 | 2/2007 | Monteleone | |
| 2007/0167385 A1 | 7/2007 | Monteleone | |
| 2009/0156539 A1 | 6/2009 | Monteleone | |
| 2010/0317719 A1 | 12/2010 | Monteleone | |
| 2011/0207795 A1 | 8/2011 | Steinbrecher et al. | |
| 2012/0015033 A1* | 1/2012 | Baroni et al. | 424/482 |
| 2012/0136043 A1 | 5/2012 | Monteleone | |
| 2013/0203839 A1 | 8/2013 | Monteleone | |
| 2014/0142163 A1 | 5/2014 | Monteleone | |
| 2014/0256788 A1 | 9/2014 | Monteleone | |
| 2015/0125523 A1 | 5/2015 | Baroni et al. | |
| 2015/0148245 A1 | 5/2015 | Monteleone et al. | |
| 2015/0211011 A1 | 7/2015 | Monteleone | |
| 2015/0218561 A1 | 8/2015 | Monteleone | |
| 2015/0232854 A1 | 8/2015 | Baroni et al. | |
| 2015/0315573 A1 | 11/2015 | Monteleone et al. | |
| 2015/0337312 A1 | 11/2015 | Monteleone | |
| 2016/0177306 A1 | 6/2016 | Monteleone | |
| 2016/0222383 A1 | 8/2016 | Baroni et al. | |
| 2016/0304876 A1 | 10/2016 | Monteleone | |
| 2017/0107520 A1 | 4/2017 | Baroni et al. | |
| 2017/0233736 A1 | 8/2017 | Monteleone et al. | |
| 2017/0240893 A1 | 8/2017 | Monteleone | |
| 2017/0253880 A1 | 9/2017 | Monteleone | |

FOREIGN PATENT DOCUMENTS

| | | |
|---|---|---|
| WO | WO-2003037368 | 5/2003 |
| WO | WO-2004087920 A1 | 10/2004 |
| WO | WO-2005014011 A1 | 2/2005 |
| WO | WO-2010054826 A1 | 5/2010 |
| WO | WO-2013037970 A1 | 3/2013 |
| WO | WO-2013158868 A1 | 10/2013 |
| WO | WO-2014140333 A1 | 9/2014 |
| WO | WO-2015/169966 A2 | 11/2015 |
| WO | WO-2016/059239 A1 | 4/2016 |
| WO | WO-2016/059243 A2 | 4/2016 |
| WO | WO-2017/055611 A2 | 4/2017 |
| WO | WO-2017/144689 A1 | 8/2017 |

OTHER PUBLICATIONS

Gillen et al., GUT, 35: 1590-1592 (1994).*
Boulay et al., International Journal of Cancer, 104: 446-449 (2003).*
Pubmed, ID 23435373, showing epub date, accessed at www.ncbi.nlm.gov/pubmed Mar. 20, 2017.*
Gemoll et al., Oncotarget, 8: 54939-54950 (2017).*
Read et al., American Family Physician, 59: 3083-3092 (1999) downloaded from http://www.aafp.org/afp/1999/0601/p3083.html.*
"Sporadic (Nonhereditary) Colorectal Cancer" downloaded from http://www.hopkinsmedicine.org/gastroenterology_hepatology/_pdfs/small_large_intestine/sporadic_nonhereditary_colorectal_cancer.pdf (2013), Oct. 16, 2017.*
De la Chapelle, Nature Reviews, 4: 769-780 (2004).*
Stolfi et al., Int. J. Mol. Sci. 14: 17972-17985 (2013).*
Chan et al., Clinical and Experimental Pharmacology and Physiology, 33: 533-540 (2006).*
Al-Sohaily et al., Journal of Gastroenterology and Hepatology, 27: 1423-1431 (2012).*
Cripps et al., Clinical Cancer Research, 8: 2188-2192 (2002).*
Kole et al., Nature Reviews, 11: 125-140 (2012).*
Monteleone et al., NEJM, 372: 1104-1113 (2015).*

(Continued)

*Primary Examiner* — Bethany P Barham
*Assistant Examiner* — Lisbeth C. Robinson
(74) *Attorney, Agent, or Firm* — Goodwin Procter LLP

(57) ABSTRACT

Disclosed herein are methods for treating/and or preventing colorectal cancer using a specific inhibitor of SMAD7 expression or function. Also disclosed are pharmaceutical compositions containing an inhibitor of SMAD7 for treating and/or preventing colorectal cancer and manufacture of medicaments containing an inhibitor of SMAD7 to be used in treating and/or preventing colorectal cancer.

13 Claims, 7 Drawing Sheets
(4 of 7 Drawing Sheet(s) Filed in Color)

(56) References Cited

OTHER PUBLICATIONS

Baker, et al. (1989) "Chromosome 17 Deletions and p53 Gene Mutations in Colorectal Carcinomas," *Science* 244:217-221.
Boulay, et al. (2001) "Combined Copy Status of I8q2I Genes in Colorectal Cancer Shows Frequent Retention of SMAD7," *Genes, Chromosomes & Cancer* 31:240-247.
American Cancer Society (2012) "Cancer Prevention & Early Detection Facts & Figures 2012," 64 pages.
Ciardiello, et al. (1991) "Differential Expression of Epidermal Growth Factor-Related Proteins in Human Colorectal Tumors," *Proc. Natl. Acad. Sci. USA*, 88:7792-7796.
Halder, et al. (2008) "Smad7 Induces Hepatic Metastasis in Colorectal Cancer," *British Journal of Cancer* 99:957-965.
International Search Report for PCT/EP2014/055195, dated Jun. 16, 2014 (5 pages).
Li, et al.(2013) "MicroRNA-25 Functions as a Potential Tumor Suppressor in Colon Cancer by Targeting Smad7" *Cancer Letters* 335:168-174.
Markowitz, et al. (2009) Author Manuscript for "Molecular Origins of Cancer: Molecular Basis of Colorectal Cancer," *N. Engl. J. Med.* 361(25): 2449-2460.
Reya, et al. (2005) "Wnt Signalling in Stem Cells and Cancer," *Nature* 434:843-850.
Rizzo, et al., (2011) "Smad7 Expression in T cells Prevents Colitis-Associated Cancer," *Cancer Research* 71:7423-7432.
Rychahou, et al. (2006) "Targeted Molecular Therapy of the PI3K Pathway Therapeutic Significance of PI3K Subunit Targeting in Colorectal Carcinoma" *Annals of Surgery* 243(6):833-842.
Siegel, et al. (2012) "Cancer Treatment and Survivorship Statistics, 2012," *CA Cancer J. Clin.* 62:220-241.
Soreide, et al. (2011) "Advances in the Understanding and Treatment of Colorectal Cancer," *Discovery Medicine* 12(66):393-404.
Stolfi, et al. (2014) "A Functional Role for Smad7 in Sustaining Colon Cancer Cell Growth and Survival," *Cell Death and Disease* 5:e1073, 1-10.
Written Opinion for PCT/EP2014/055195, dated Jun. 16, 2014 (7 pages).
Yang, et al. (2011) "Synchronous Colorectal Cancers: A Review of Clinical Features, Diagnosis, Treatment, and Prognosis," *Dig. Surg.* 28:379-385.
Broderick P et al.,(2007) 'A Genome-Wide Association Study Shows that Common Alleles of SMAD7 Influence Colorectal Cancer Risk,' Nat Genet, 39(11):1315-7 (Abstract).
National Cancer Institute. Bethesda, MD. Howlader et al. (eds). (2011) "SEER Cancer Statistics Review, 1975-2008" [database online] Retrieved from <http://seer.cancer.gov/archive/csr/1975_2008/>. Table 1.11: Median Age of Cancer Patients at Diagnosis, 2004-2008 by Primary Cancer site, Race and Sex (2 pages).
Pittman AM et al., (2009) 'The Colorectal Cancer Risk at 18q21 is Caused by a Novel Variant Altering SMAD7 Expression,' Genome Res, 19(6):987-93.
Li et al., (2013), 'MicroRNA-25 Functions as a Potential Tumor Suppressor in Colon Cancer by Targeting Smad7,' Can Lett, Feb. 19, 2013 (Feb. 19, 2013), 335(1):1-2, Appendix A, Supplementary Data, retrieved from the internet at <http://www.sciencedirect.com/science/article/pii/S0304383513001559>.
Mundade R et al., (2014), 'Genetic Pathways, Prevention, and Treatment of Sporadic Colorectal Cancer,' Oncoscience, 1(6):400-6.
Yamagishi H et al., (2016), 'Molecular Pathogenesis of Sporadic Colorectal Cancers,' Chin J Cancer, 35:4 (8 pages).

\* cited by examiner

A

B

C

D

A

B

C

D

METHODS OF TREATING COLORECTAL CANCER

CROSS REFERENCE TO RELATED APPLICATIONS

This application claims the benefit of U.S. provisional application 61/790,488, filed Mar. 15, 2013, the entire contents of which are herein incorporated by reference.

FIELD OF THE INVENTION

The present invention is generally directed towards methods of treating and/or preventing colorectal cancer and colorectal cancer cell growth via administration of SMAD7 inhibitors, particularly antisense oligonucleotides directed against SMAD7, as well as pharmaceutical compositions containing SMAD7 inhibitors for use in treating colorectal cancer.

BACKGROUND

Colorectal cancer is a disease characterized by unchecked proliferation of cells of the large intestine, including cells of the colon or rectum. Colorectal cancer tumors are believed to originate in normal mucosa. Tumorigenesis is associated with the appearance of clusters of enlarged crypts showing proliferative and biochemical abnormalities. Proliferation of the epithelial cells that carry the causative mutation or mutations can become early stage tumors characterized by high-grade dysplasia. Further growth can result in invasive growth into the muscle layers and through the bowel wall. If untreated, these tumors can spread to regional lymph nodes and then metastasize to distant sites, at which point they become largely untreatable using currently available technologies (Markowitz and Bertagnolli (2009) *N. Engl. J. Med.* 361(25): 2449-2460). While tumors can arise de novo, evidence indicates that approximately 60% of carcinomas originate from pre-existing adenomas (Soreide et al., (2011) *Discov. Med.* 12(66):393-404). Thus, the vast majority of colorectal cancer tumors can be classified as adenocarcinomas, but lymphomas and squamous cell carcinomas are also observed in a smaller subset of cases. Genetic mutations that result in carcinogenesis include mutations in members of the Wnt signaling pathway, members of the TGF-β cell signaling pathway such as TGF-β1 and SMAD family members, proteins that regulate the balance between cell proliferation and cell death such as TP53, and other proteins such as DCC (Reya and Clevers (2005) *Nature* 434(7035):843-850; Baker et al., (1989) *Science* 244:217-221; Markowitz and Bertagnolli, supra). Abnormal PI3K/Akt activation and downstream mTOR signaling are associated with colorectal cancer tumorigenesis (Rychahou et al., (2006) *Ann. Surg.* 243 (6):833-842). High levels of EGFR expression have also been observed in colon cancer cell lines and are correlated with colorectal cancer tumor progression (Ciardiello et al., (1991) *Proc. Natl. Acad. Sci. USA* 88(17):7792-7796). Beyond familial and genetic factors, risk factors for colorectal cancer may include low levels of physical activity, alcohol consumption, high dietary intake of fat and meat and low intake of fiber and vegetables. Symptoms of colorectal cancer typically include rectal bleeding, anemia, constipation, blood in the stool, weight loss, fever, loss of appetite, and nausea or vomiting.

Colorectal cancer is the second most common form of cancer among American male and female survivors of cancer (Siegel et al., (2012) *CA Cancer J. Clin.* 62(4):220-41). Additionally, colorectal cancer is among the top three most common causes of cancer death in the Western world (Soreide et al., (2011) *Discov. Med.* 12(66):393-404). The more recent adaptation of many Asian countries to a Western lifestyle has also resulted in a significant increase in colorectal cancer in those populations (Yang et al., (2011) *Dig. Surg.* 28(5-6):379-385). In 2012, it is estimated that there were 1.2 million individuals in the United States living with a previous diagnosis of colorectal cancer. For the same year, it was predicted that an additional 143,460 would be diagnosed with the disease. The median age at diagnosis of colorectal cancer is 68 years for males and 72 years for females (Howlader et al., (2011) *SEER Cancer Statistics Review*, 1975-2008. Bethesda, Md.: National Cancer Institute). While incidence of colorectal cancer is not rare in elderly adults, only 59.1% of individuals over the age of 50 receive colorectal cancer screening according to guidelines (American Cancer Society (2012) *Cancer Prevention & Early Detection Facts & Figures*. Atlanta, Ga.: American Cancer Society). This lack of early detection results in only 39% of patients being diagnosed when the cancer has not progressed past a local stage (Howlader et al., supra). Given the increasing number of patients suffering from colorectal cancer, there is a need for development of robust treatment methods, especially for the large number of patients who are not identified by early screening.

SUMMARY

The invention described herein provides novel methods for treating colorectal cancer via inhibition of SMAD7, leveraging the role of SMAD7 as a key antagonist of the TGF-β signaling pathway. While other potential targets for therapeutic intervention in colorectal cancer have been proposed, the present invention provides a new treatment shown to prevent, retard, stop, or reverse colorectal tumor cell growth.

The present invention provides a method for treating colorectal cancer by inhibiting SMAD7. Specifically, the invention provides a method of inhibiting SMAD7 in a colorectal tumor in a patient. The invention also provides a method of inhibiting growth of colorectal cancer cells by inhibiting SMAD7. The invention also provides a method for inhibiting SMAD7, treating colorectal cancer, and/or inhibiting growth of colorectal cancer cells via administration of an effective amount of an inhibitor of SMAD7. For example, inhibitors of SMAD7 (e.g., anti-SMAD7 antisense therapies, i.e., antisense oligonucleotide against SMAD7, and antibodies against SMAD7). "Antisense oligonucleotide," as used herein, refers to a short synthetic oligonucleotide sequence complementary to the messenger RNA (mRNA), which encodes for the target protein (e.g., SMAD7). Antisense oligonucleotide sequences hybridize to the mRNA producing a double-strand hybrid that can lead to the activation of ubiquitary catalytic enzymes, such as RNase H, which degrades DNA/RNA hybrid strands thus preventing protein translation.

An inhibitor of SMAD7 may be a specific inhibitor of SMAD7 such as an antisense oligonucleotide or any other means of targeting SMAD7 with a high degree of specificity. An antisense oligonucleotide inhibitor of SMAD7 may be selected from, but is not limited to, the group of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12, described herein. For example, an antisense oligonucleotide inhibitor of SMAD7 may include SEQ ID NO: 5 or SEQ ID NO: 9, or may include SEQ ID NO: 6 or SEQ ID NO: 10. An exemplary SMAD7 antisense oligonucleotide of the present invention is the sequence represented by a form of SEQ ID NO: 6, in which all phosphate bonds are phosphorothioate bonds (SEQ ID NO: 10, referred to herein as GED-0301).

"Inhibitor," as used herein, refers to an agent capable of decreasing expression of a gene or DNA sequence, preventing or suppressing production, activity, or translation of an RNA product of a gene into protein, or preventing or suppressing the activity of the protein product of a gene, through either a direct or indirect interaction with the gene, RNA product, or protein product of a gene or any transitional forms of these entities or another molecular entity whose activity or expression impinges upon the activity or expression of the intended target. Such inhibitors may include, but are not limited to, for example, antibodies, small molecules that bind to a specific molecular target, and antisense oligonucleotides targeted to specific mRNA transcripts. Accordingly, "inhibitor of SMAD7," as used herein, refers to an agent capable of decreasing expression of SMAD7, preventing or suppressing production, activity, or translation of an RNA product of SMAD7 into protein, or preventing or suppressing the activity of the protein product of SMAD7, through either a direct or indirect interaction with the gene, RNA product, or protein product of SMAD7 or any transitional forms of these entities or another molecular entity whose activity or expression impinges upon the activity or expression of SMAD7.

The present invention also provides for methods of treating colorectal cancer via administering specific inhibitors of SMAD7. A "specific inhibitor," as used herein, refers to an agent that has structural and/or functional properties that allow it to exclusively or with a high degree of selectivity act upon a molecular target. Thus, a specific inhibitor of SMAD7 possesses the inherent functional property of targeting the SMAD7 gene, its RNA or protein products, or another molecular entity whose activity or expression impinges upon the activity or expression of SMAD7 or its products either exclusively or with a high degree of specificity. In the case of antibody inhibitors of SMAD7, specificity can be engineered into the antibody via inclusion of protein sequences known to bind SMAD7 protein epitopes with a high degree of specificity. In the case of small molecule inhibitors of SMAD7, chemical groups can be included in the formulation of the small molecule that allow binding to specific features of SMAD7 protein. Antisense oligonucleotides can be designed such that the targeting portion of the incorporated nucleotide sequence of each antisense oligonucleotide is completely or almost completely complementary to the SMAD7 mRNA sequence. Incorporation of such complementary or nearly complementary nucleotide sequences allows one to engineer antisense oligonucleotides with a high degree of specificity for a given target. Specificity can be assessed via measurement of parameters such as dissociation constant, or other criteria such as changes in protein or RNA expression levels or other assays that measure SMAD7 activity or expression.

Specific SMAD7 inhibitors can include, for example, small binding molecules, e.g., natural and synthetic compounds, antibodies, aptamers, intramers, RNAi (double stranded RNA, siRNA) and anti-SMAD7 antisense molecules for treating colorectal cancer and/or inhibiting colorectal cancer cell growth. SMAD7 inhibitors may also comprise truncated and/or mutated SMAD7 molecules which interfere with SMAD7 activity, binding partners, or substrates and which, thereby, inhibit SMAD7 function.

"Effective amount," as used herein, refers to the amount of an agent that is sufficient to at least partially treat a condition when administered to a patient. The therapeutically effective amount will vary depending on the condition, the route of administration of the component, and the age, weight, etc. of the patient being treated. Accordingly, an effective amount of a specific inhibitor of SMAD7 is the amount of inhibitor necessary to treat colorectal cancer in a patient such that administration of the agent prevents the colorectal cancer from occurring in a subject, prevents colorectal cancer progression (e.g., prevents onset of events such as tumorigenesis, tumor growth, or metastasis), or relieves or completely ameliorates all associated symptoms of the colorectal cancer, i.e. causes regression of the disease.

The present invention also provides a method for treating colorectal cancer via administration of a pharmaceutical composition comprising an antisense oligonucleotide against SMAD7. In another aspect, the invention provides a pharmaceutical composition for use in treating colorectal cancer. The pharmaceutical composition may be comprised of an inhibitor of SMAD7, such as an antisense oligonucleotide that targets SMAD7, and a pharmaceutically acceptable carrier. As used herein the term "pharmaceutical composition" means, for example, a mixture containing a specified amount of a therapeutic compound, e.g. a therapeutically effective amount, of a therapeutic compound in a pharmaceutically acceptable carrier to be administered to a mammal, e.g., a human, in order to treat colorectal cancer. In some embodiments, contemplated herein are pharmaceutical compositions comprising a contemplated antisense oligonucleotide against SMAD7 and a pharmaceutically acceptable carrier. In another aspect, the invention discloses use of an antisense oligonucleotide against SMAD7 in the manufacture of a medicament for treating colorectal cancer. "Medicament," as used herein, has essentially the same meaning as the term "pharmaceutical composition."

As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art. In one embodiment the pharmaceutical composition is administered orally and includes an enteric coating suitable for regulating the site of absorption of the encapsulated substances within the digestive system or gut. For example, an enteric coating can include an ethylacrylate-methacrylic acid copolymer.

In one embodiment, a contemplated antisense oligonucleotide against SMAD7 and any pharmaceutical composition thereof may be administered by one or several routes, including orally, topically, parenterally, e.g., subcutaneous injection, by inhalation spray, or rectally. The term parenteral as used herein includes subcutaneous injections, intrapancreatic administration, intravenous, intramuscular, intraperitoneal, intrasternal injection or infusion techniques. For example, the antisense oligonucleotide against SMAD7 may be administered subcutaneously to a subject. In another example, the antisense oligonucleotide against SMAD7 may be administered orally to a subject. In another example, the antisense oligonucleotide against SMAD7 may be administered directly to a colorectal tumor or colorectal cancer cells via parenteral administration.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Colorectal Cancer

Figure 1:
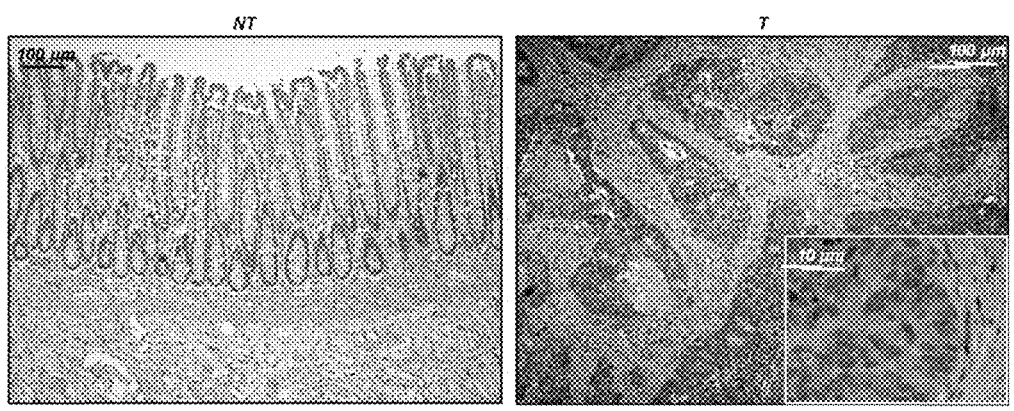
FIG. 1(A) shows SMAD7 immunostaining in non-tumoral (NT) and tumoral (T) areas of a patient with sporadic colorectal cancer.
FIG. 1(B) is a Western blot showing SMAD7 and β-actin levels in NT and T tissue from two patients with sporadic colorectal cancer.
FIG. 1(C) is a Western blot showing SMAD7 and β-actin levels in IECs and DLD-1 and HCT-116 cells.
FIG. 1(D) is a Western blot showing expression levels of SMAD7 and β-actin in four colorectal cancer cell lines (HCT-116, HCT-115, HT-29, and DLD-1) and one hepatocellular carcinoma cell line (HepG2).
Figure 1:
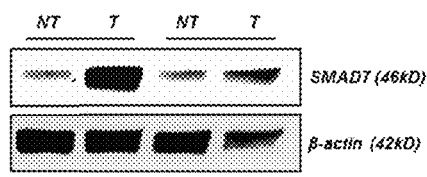
Figure 1:
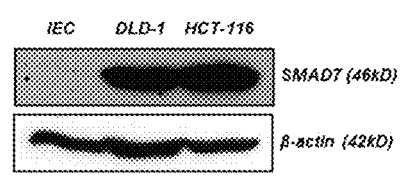
Figure 1:
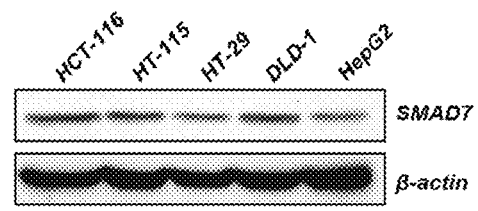

The present invention provides methods for treatment of colorectal cancer. "Colorectal cancer," as used herein, refers to a disease characterized by unchecked proliferation of cells of the large intestine, including cells of the colon or rectum. Colorectal cancer typically originates in epithelial cells of the large intestine with intestinal crypt stem cells being a likely cell of origin. Genetic mutations that result in carcinogenesis include mutations in members of the Wnt signaling pathway such as β-catenin, APC, AXIN1, AXIN2, TCF7L2, and NKD1, members of the TGF-β cell signaling pathway such as TGF-β1 and SMAD family members, proteins that regulate the balance between cell proliferation and cell death such as TP53, and other proteins such as DCC. Proliferation of the epithelial cells that carry the causative mutation or mutations can result in invasive growth into the muscle layers and through the bowel wall. Symptoms of colorectal cancer typically include rectal bleeding, anemia, constipation, blood in the stool, weight loss, fever, loss of appetite, and nausea or vomiting. The vast majority of colorectal cancer tumors can be classified as adenocarcinomas while lymphomas and squamous cell carcinomas are observed in a smaller subset of cases. Accordingly, the term "colorectal tumor," as used herein, refers to any abnormal malignant growth of tissue associated with cells originating in the large intestine or colorectal cancer pathology.

The term "colorectal cancer cells," as used herein, refers to any cell of origin giving rise to colorectal cancer or a colorectal tumor, a cell associated with the tumorigenesis, growth, evolution, maintenance, or support of a colorectal tumor, or any other cell associated with the pathological manifestation of colorectal cancer. "Growth of colorectal cancer cells," as used herein, refers to the unchecked or abnormal proliferation of cells associated with a colorectal cancer cell of origin, a colorectal tumor cell, or any cell associated with the manifestation of colorectal cancer pathology. Growth of colorectal cancer cells may be the result of abnormal cell cycle activity, failure to induce cell cycle checkpoints, failure to induce apoptosis, or loss of other tumor suppressor activities.

Treatment and Evaluation

The terms "treat", "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Efficacy of treatment may be evaluated by means of evaluation of gross symptoms associated with colorectal cancer, analysis of tissue histology, biochemical assay, imaging methods such as, for example, magnetic resonance imaging, or other known methods. For instance, efficacy of treatment may be evaluated by analyzing anemic state, rectal bleeding, tumor size, or other aspects of gross pathology associated with colorectal cancer following administration of a SMAD7 inhibitor to a colorectal cancer patient. Efficacy of treatment may also be evaluated at the tissue or cellular level, for example, by means of obtaining a tissue or tumor biopsy and evaluating gross tissue or cell morphology or staining properties. Biochemical assays that examine protein or RNA expression may also be used to evaluate efficacy of treatment. For instance, one may evaluate PCNA, p-CDK2 (Thr-14/Tyr-15), or levels of another protein indicative of cell proliferation or cell death activity in dissociated cells or non-dissociated tissue via immunocytochemical, immunohistochemical, or Western blotting methods. One may also evaluate the presence or level of expression of useful biomarkers found in plasma or tumoral or non-tumoral tissue to evaluate cancer progression and efficacy of treatment.

In evaluating efficacy of treatment, suitable controls may be chosen to ensure a valid assessment. For instance, one can compare symptoms evaluated in a patient with colorectal cancer following administration of an inhibitor of SMAD7 to those symptoms in the same patient prior to treatment or in another patient not diagnosed with colorectal cancer. Alternatively, one may compare the results of biochemical or histological analysis of tumoral tissue following administration of a SMAD7 inhibitor with those of non-tumoral tissue from the same patient or from an individual not diagnosed with colorectal cancer or from the same patient prior to administration of the SMAD7 inhibitor.

Validation of SMAD7 inhibition may be determined by direct or indirect assessment of SMAD7 expression levels or activity. For instance, biochemical assays that measure SMAD7 protein or RNA expression may be used to evaluate overall SMAD7 inhibition. For instance, one may measure SMAD7 protein levels in tumor tissue by Western blot to evaluate overall SMAD7 levels. One may also measure SMAD7 mRNA levels by means of Northern blot or quantitative polymerase chain reaction to determine overall SMAD7 inhibition. One may also evaluate SMAD7 protein levels or levels of another protein indicative of SMAD7 activity in dissociated cells or non-dissociated tissue via immunocytochemical or immunohistochemical methods. SMAD7 inhibition may also be evaluated indirectly by measuring parameters such as cell cycle phase distribution, staining with markers of cell death such as Annexin V or Caspase III, or measuring alteration in other parameters correlated with changes in SMAD7 activity. For instance, one may measure levels of active caspase-3 in cells of a tumor treated with a SMAD7 inhibitor as an indication of SMAD7 activity in said cells. One may also evaluate the presence or level of expression of useful biomarkers found in plasma or tumoral or non-tumoral tissue to evaluate efficacy of SMAD7 inhibition.

In evaluating efficacy of SMAD7 knockdown, suitable controls may be chosen to ensure a valid assessment. For instance, one may compare the results of biochemical or histological analysis of tumoral tissue following administration of a SMAD7 inhibitor with those of non-tumoral tissue from the same patient or from an individual not diagnosed with colorectal cancer or from the same patient prior to administration of the SMAD7 inhibitor.

A "patient," as described herein, refers to any animal at risk for or suffering from colorectal cancer, including, but not limited to, mammals, primates, and humans. For example, a patient may be an individual diagnosed with a high risk of colorectal cancer development or someone who has been diagnosed with colorectal cancer. In certain embodiments, the patient may be a non-human mammal such as, for example, a cat, a dog, or a horse.

Inhibitors of SMAD7

In certain embodiments, an anti-SMAD7 antisense oligonucleotide may target site 403, 233, 294, 295, 296, 298, 299, and/or 533 (i.e., nucleotides 403, 233, 294, 295, 296, 298, 299, and 533, respectively) of the human SMAD7 mRNA. In an exemplary embodiment, the anti-SMAD7 antisense oligonucleotide targets nucleic acids 403-423 of human SMAD7 mRNA. Exemplary SMAD7 inhibitors include those disclosed in PCT Publication No. WO2010/054826, which is hereby incorporated by reference in its entirety.

In certain embodiments, an antisense oligonucleotide may be derived from the following anti-SMAD7 antisense oligonucleotide 5'-GTCGCCCCTTCTCCCCGCAGC-3' (SEQ ID NO: 3).

It is contemplated herein that an antisense oligonucleotide targeting SMAD7 may comprise a mixed-backbone wherein the cytosine residues in a CpG pair are replaced by 5'-methylcytosine (abbreviated as Me-dC). Methylphosphonate linkages may also be placed at the 5' and/or 3' ends of an antisense oligonucleotide (abbreviated as MeP). The phosphate backbone of a contemplated anti-SMAD7 antisense oligonucleotide may optionally include 1, 2, 3, 4 or more phosphorothioate bonds (e.g., phosphorothioate bonds would replace phosphodiester bonds). In an embodiment, all phosphate bonds may be phosphorothioate bonds.

Exemplary antisense oligonucleotide therapies that target SMAD7 include, but are not limited to:

5'-GTXYCCCCTTCTCCCXYCAG-3' (SEQ ID NO: 4), wherein X is a nucleotide comprising a nitrogenous base selected from the group consisting of cytosine and 5-methylcytosine or a 2'-O-methylcytosine nucleoside, and wherein Y is a nucleotide comprising a nitrogenous base selected from the group consisting of guanine and 5-methylguanine or a 2'-O-methylguanine nucleoside, provided that at least one of the nucleotides X or Y comprises a methylated nitrogenous base;

5'-GTXGCCCCTTCTCCCXGCAG-3' (SEQ ID NO: 5), wherein X is 5-methyl 2'-deoxycytidine 5'-monophosphate;

5'-GTXGCCCCTTCTCCCXGCAGC-3' (SEQ ID NO: 6), wherein X is 5-methyl 2'-deoxycytidine 5'-monophosphate;

5'-ZTXGCCCCTTCTCCCXGCAZ-3' (SEQ ID NO: 7), wherein X is 5-methyl 2'-deoxycytidine 5'-monophosphate and Z is 2'-deoxyguanosine methylphosphonate;

5'-ZTXGCCCCTTCTCCCXGCAZC-3' (SEQ ID NO: 8), wherein X is 5-methyl 2'-deoxycytidine 5'-monophosphate and Z is 2'-deoxyguanosine methylphosphonate.

In a particular embodiment, contemplated SMAD7 antisense may be a sequence comprising one of:

5'-GTXGCCCCTTCTCCCXGCAG-3' (SEQ ID NO: 9), wherein X is 5-methyl 2'-deoxycytidine 5'-monophosphorothioate;

5'-GTXGCCCCTTCTCCCXGCAGC-3' (SEQ ID NO: 10), wherein X is 5-methyl 2'-deoxycytidine 5'-monophosphorothioate;

5'-ZTXGCCCCTTCTCCCXGCAZ-3' (SEQ ID NO: 11), wherein X is 5-methyl 2'-deoxycytidine 5'-monophosphate and Z is 2'-deoxyguanosine methylthiophosphonate;

5'-ZTXGCCCCTTCTCCCXGCAZC-3' (SEQ ID NO: 12), wherein X is 5-methyl 2'-deoxycytidine 5'-monophosphate and Z is 2'-deoxyguanosine methylthiophosphonate.

For example, SEQ ID NOs. 9-12 include 1, 2, 3, 4 or more phosphorothioate bonds. In an embodiment, all O,O phosphonate bonds of SEQ ID NOs. 9-12 are phosphorothioate bonds.

Pharmaceutical Compositions and Routes of Administration

Pharmaceutical compositions containing an antisense oligonucleotide against SMAD7, such as those disclosed herein, can be presented in a dosage unit form and can be prepared by any suitable method. A pharmaceutical composition should be formulated to be compatible with its intended route of administration. Useful formulations can be prepared by methods well known in the pharmaceutical art. For example, see *Remington's Pharmaceutical Sciences*, 18th ed. (Mack Publishing Company, 1990).

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Parenteral Administration

The pharmaceutical compositions of the invention can be formulated for parenteral administration, e.g., formulated for injection via the intravenous, intramuscular, subcutaneous, intralesional, or intraperitoneal routes. The preparation of an aqueous composition, such as an aqueous pharmaceutical composition containing a SMAD7 inhibitor, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. In addition, sterile, fixed oils may be employed as a solvent or suspending medium. For this purpose any bland fixed oil can be employed including synthetic mono- or diglycerides. In addition, fatty acids such as oleic acid can be used in the preparation of injectables. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In one embodiment, the SMAD7 inhibitor may be suspended in a carrier fluid comprising 1% (w/v) sodium carboxymethylcellulose and 0.1% (v/v) TWEEN™ 80. Under ordinary conditions of storage and use, these preparations contain a preservative to prevent the growth of microorganisms.

Injectable preparations, for example, sterile injectable aqueous or oleaginous suspensions may be formulated according to the known art using suitable dispersing or wetting agents and suspending agents. Generally, dispersions are prepared by incorporating the various sterilized active ingredients into a sterile vehicle which contains the basic dispersion medium and the required other ingredients from those enumerated above. Sterile injectable solutions of the invention may be prepared by incorporating a SMAD7 inhibitor in the required amount of the appropriate solvent with various of the other ingredients enumerated above, as required, followed by filtered sterilization. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The injectable formulations can be sterilized, for example, by filtration through a bacteria-retaining filter.

The preparation of more, or highly, concentrated solutions for intramuscular injection is also contemplated. In this regard, the use of DMSO as solvent is preferred as this will result in extremely rapid penetration, delivering high concentrations of the SMAD7 inhibitor to a small area.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium 10 carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

In an exemplary embodiment, a pharmaceutical composition for subcutaneous administration of an antisense oligonucleotide against SMAD7 comprises an antisense oligonucleotide such as that represented by SEQ ID NO: 6, or a pharmaceutically acceptable salt thereof (such as a sodium salt), and a pharmaceutically acceptable carrier.

Oral Administration

In some embodiments, contemplated herein are compositions suitable for oral delivery of an antisense oligonucleotide, e.g., tablets, that include an enteric coating, e.g., a gastro-resistant coating, such that the compositions may deliver the antisense compound to, e.g., the colon of a patient. For example, such administration may result in a topical effect, substantially topically applying the antisense compound directly to an affected portion of the colon of a patient. Such administration, may, in some embodiments, substantially avoid unwanted systemic absorption of the antisense compound.

For example, a tablet for oral administration is provided that comprises granules (e.g., is at least partially formed from granules) that include a disclosed antisense compound, e.g., GED-0301, and pharmaceutically acceptable excipients. Such a tablet may be coated with an enteric coating. Contemplated tablets may include pharmaceutically acceptable excipients such as fillers, binders, disintegrants, and/or lubricants, as well as coloring agents, release agents, coating agents, sweetening, flavoring such as wintergreen, orange, xylitol, sorbitol, fructose, and maltodextrin, and perfuming agents, preservatives and/or antioxidants.

In some embodiments, contemplated pharmaceutical formulations include an intra-granular phase that includes a contemplated antisense compound, e.g. GED-0301, or a pharmaceutically acceptable salt, e.g., GED-0301 and a pharmaceutically acceptable filler. For example, GED-0301 and a filler may be blended together, optionally, with other excipients, and formed into granules. In some embodiments, the intragranular phase may be formed using wet granulation, e.g. a liquid (e.g., water) is added to the blended antisense compound and filler, and then combination is dried, milled and/or sieved to produce granules. One of skill in the art would understand that other processes may be used to achieve an intragranular phase.

In some embodiments, contemplated formulations include an extra-granular phase, which may include one or more pharmaceutically acceptable excipients, and which may be blended with the intragranular phase to form a disclosed formulation.

A disclosed formulation may include an intragranular phase that includes a filler. Exemplary fillers include, but are not limited to, cellulose, gelatin, calcium phosphate, lactose, sucrose, glucose, mannitol, sorbitol, microcrystalline cellulose, pectin, polyacrylates, dextrose, cellulose acetate, hydroxypropylmethyl cellulose, partially pregelatinized starch, calcium carbonate, and others including combinations thereof.

In some embodiments, a disclosed formulation may include a intragranular phase and/or a extragranular phase that includes a binder, which may generally function to hold the ingredients of the pharmaceutical formulation together. Exemplary binders of the invention may include, but are not limited to, the following: starches, sugars, cellulose or modified cellulose such as hydroxypropyl cellulose, lactose, pregelatinized maize starch, polyvinyl pyrrolidone, hydroxypropyl cellulose, hydroxypropylmethyl cellulose, low substituted hydroxypropyl cellulose, sodium carboxymethyl cellulose, methyl cellulose, ethyl cellulose, sugar alcohols and others including combinations thereof.

Contemplated formulations, e.g., that include an intragranular phase and/or an extragranular phase, may include a disintegrant such as but are not limited to, starch, cellulose, crosslinked polyvinyl pyrrolidone, sodium starch glycolate, sodium carboxymethyl cellulose, alginates, corn starch, crosmellose sodium, crosslinked carboxymethyl cellulose, low substituted hydroxypropyl cellulose, acacia, and others including combinations thereof. For example, an intragranular phase and/or an extragranular phase may include a disintegrant.

In some embodiments, a contemplated formulation includes an intra-granular phase comprising a disclosed antisense compound and excipients chosen from: mannitol, microcrystalline cellulose, hydroxypropylmethyl cellulose, and sodium starch glycolate or combinations thereof, and an extra-granular phase comprising one or more of: microcrystalline cellulose, sodium starch glycolate, and magnesium stearate or mixtures thereof.

In some embodiments, a contemplated formulation may include a lubricant, e.g. an extra-granular phase may contain a lubricant. Lubricants include but are not limited to talc, silica, fats, stearin, magnesium stearate, calcium phosphate, silicone dioxide, calcium silicate, calcium phosphate, colloidal silicon dioxide, metallic stearates, hydrogenated vegetable oil, corn starch, sodium benzoate, polyethylene glycols, sodium acetate, calcium stearate, sodium lauryl sulfate, sodium chloride, magnesium lauryl sulfate, talc, and stearic acid.

In some embodiments, the pharmaceutical formulation comprises an enteric coating. Generally, enteric coatings create a barrier for the oral medication that controls the location at which the drug is absorbed along the digestive track. Enteric coatings may include a polymer that disintegrates a different rates according to pH. Enteric coatings may include for example, cellulose acetate phthalate, methyl acrylate-methacrylic acid copolymers, cellulose acetate succinate, hydroxylpropylmethyl cellulose phthalate, methyl methacrylate-methacrylic acid copolymers, ethylacrylate-methacrylic acid copolymers, methacrylic acid copolymer type C, polyvinyl acetate-phthalate, and cellulose acetate phthalate.

Exemplary enteric coatings include Opadry® AMB, Acryl-EZE®, Eudragit® grades. In some embodiments, an enteric coating may comprise about 5% to about 10%, about 5% to about 20%, 8 to about 15%, about 8% to about 18%, about 10% to about 12%, or about 12 to about 16%, of a contemplated tablet by weight. For example, enteric coatings may include an ethylacrylate-methacrylic acid copolymer.

For example, a tablet is provided that comprises or consists essentially of about 0.5% to about 70%, e.g. about 0.5% to about 10%, or about 1% to about 20%, by weight of an antisense oligonucleotide or a pharmaceutically acceptable salt thereof (e.g. GED-0301). Such a tablet may include for example, about 0.5% to about 60% by weight of mannitol, e.g. about 30% to about 50% by weight mannitol, e.g. about 40% by weight mannitol; and/or about 20% to about 40% by weight of microcrystalline cellulose, or about 10% to about 30% by weight of microcrystalline cellulose. For example, a disclosed tablet may comprise an intragranular phase that includes about 30% to about 60%, e.g. about 45% to about 65% by weight, or alternatively, about 5 to about 10% by weight GED-0301, about 30% to about 50%, or alternatively, about 5% to about 15% by weight mannitol, about 5% to about 15% microcrystalline cellulose, about 0% to about 4%, or about 1% to about 7% hydroxypropylmethylcellulose, and about 0% to about 4%, e.g. about 2% to about 4% sodium starch glycolate by weight.

In another embodiment, a pharmaceutical tablet formulation for oral administration of an antisense oligonucleotide against SMAD7 comprises an intra-granular phase, wherein the intra-granular phase includes an antisense oligonucleotide such as GED-0301, or a pharmaceutically acceptable salt thereof (such as a sodium salt), and a pharmaceutically acceptable filler, and which may also include an extra-granular phase, that may include a pharmaceutically acceptable excipient such as a disintegrant. The extra-granular phase may include components chosen from microcrystalline cellulose, magnesium stearate, and mixtures thereof. The pharmaceutical composition may also include an enteric coating of about 12% to 16% by weight of the tablet. For example, a pharmaceutically acceptable tablet for oral use may comprise about 0.5% to 10% by weight of an antisense oligonucleotide, e.g., GED-0301, or a pharmaceutically acceptable salt thereof, about 30% to 50% by weight mannitol, about 10% to 30% by weight microcrystalline cellulose, and an enteric coating comprising an ethylacrylate-methacrylic acid copolymer.

In another example, a pharmaceutically acceptable tablet for oral use may comprise an intra-granular phase, comprising about 5 to about 10% by weight of an antisense oligonucleotide, e.g., GED-0301, or a pharmaceutically acceptable salt thereof, about 40% by weight mannitol, about 8% by weight microcrystalline cellulose, about 5% by weight hydropropylmethyl cellulose, and about 2% by weight sodium starch glycolate; an extra-granular phase comprising about 17% by weight microcrystalline cellulose, about 2% by weight sodium starch glycolate, about 0.4% by weight magnesium stearate; and an enteric coating over the tablet comprising an ethylacrylate-methacrylic acid copolymer.

In some embodiments the pharmaceutical composition may contain an enteric coating comprising about 13% or about 15%, 16%, 17% or 18% by weight, e.g., AcyrlEZE® (see, e.g., PCT Publication No. WO2010/054826, which is hereby incorporated by reference in its entirety).

The rate at which point the coating dissolves and the active ingredient is released is its dissolution rate. In an embodiment, a contemplated tablet may have a dissolution profile, e.g. when tested in a USP/EP Type 2 apparatus (paddle) at 100 rpm and 37° C. in a phosphate buffer with a pH of 7.2, of about 50% to about 100% of the oligonucleotide releasing after about 120 minutes to about 240 minutes, for example after 180 minutes. In another embodiment, a contemplated tablet may have a dissolution profile, e.g. when tested in a USP/EP Type 2 apparatus (paddle) at 100 rpm and 37° C. in diluted HCl with a pH of 1.0, where substantially none of the oligonucleotide is released after 120 minutes. A contemplated tablet, in another embodiment, may have a dissolution profile, e.g. when tested in USP/EP Type 2 apparatus (paddle) at 100 rpm and 37° C. in a phosphate buffer with a pH of 6.6, of about 10% to about 30%, or not more than about 50%, of the oligonucleotide releasing after 30 minutes.

Disclosed formulations, e.g. tablets, in some embodiments, when orally administered to the patient may result in minimal plasma concentration of the oligonucleotide in the patient. In another embodiment, disclosed formulations, when orally administered to a patient, topically deliver to the colon or rectum of a patient, e.g. to an affected or diseased site of a patient.

In some embodiments, methods provided herein may further include administering at least one other agent that is directed to treatment of diseases and disorders disclosed herein. In one embodiment, contemplated other agents may be co-administered (e.g., sequentially or simultaneously).

Agents contemplated include immunosuppressive agents including glucocorticoids, cytostatics, antibodies, agents acting on immunophilins, interferons, opioids, TNF binding proteins, mycophenolate, and small biological agents. For example, contemplated immunosuppressive agents include, but are not limited to: tacrolimus, cyclosporine, pimecrolimus, sirolimus, everolimus, mycophenolic acid, fingolimod, dexamethasone, fludarabine, cyclophosphamide, methotrexate, azathioprine, leflunomide, teriflunomide, anakinra, anti-thymocyte globulin, anti-lymphocyte globulin, muromonab-CD3, afutuzumab, rituximab, teplizumab, efalizumab, daclizumab, basiliximab, adalimumab, infliximab, and etanercept.

Dosage and Frequency of Administration

Exemplary formulations include dosage forms that include or consist essentially of about 35 mg to about 500 mg of an antisense oligonucleotide against SMAD7. For example, formulations that include about 35 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, or 250 mg of an antisense oligonucleotide against SMAD7 are contemplated herein. In one embodiment, a formulation may include about 40 mg, 80 mg, or 160 mg of an antisense oligonucleotide against SMAD7. In some embodiments, a formulation may include at least 100 μg of an antisense oligonucleotide against SMAD7. For example, formulations may include about 0.1 mg, 0.2 mg, 0.3 mg, 0.4 mg, 0.5 mg, 1 mg, 5 mg, 10 mg, 15 mg, 20 mg, or 25 mg of an antisense oligonucleotide against SMAD7. The amount administered will depend on variables such as the type and extent of disease or indication to be treated, the overall health and size of the patient, the in vivo potency of the antisense oligonucleotide, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 40 mg to 160 mg. Dosing frequency can vary, depending on factors such as route of administration, dosage amount and the disease being treated. Exemplary dosing frequencies are once per day, once per week and once every two weeks. In some embodiments, dosing is once per day for 7 days.

EXAMPLES

The invention is further illustrated by the following examples. The examples are provided for illustrative purposes only, and are not to be construed as limiting the scope or content of the invention in any way.

Example 1: SMAD7 Protein Expression Levels in Colorectal Cancer Cells

SMAD7 protein expression levels were evaluated in paired colorectal cancer tumoral and non-tumoral colonic mucosal specimens taken from 6 patients undergoing colonic resection for colorectal cancer. SMAD7 immunostaining of tumoral (T) and non-tumoral (NT) tissue revealed a marked accumulation of SMAD7 protein in tumoral as compared to the non-tumoral tissue (FIG. 1A, representative of three separate experiments in which sections of six patients with colorectal cancer were analyzed). No staining was observed when colorectal cancer sections were incubated with isotype control IgG (not shown). Additionally, SMAD7 protein levels in tumoral (T) and non-tumoral (NT) tissue were evaluated by Western blotting in two colorectal cancer patients. Western blotting of cell extract demonstrated observably higher levels of SMAD7 in tumoral tissue compared to non-tumoral tissue (FIG. 1B). β-actin was used as a loading control.

SMAD7 protein expression was also investigated in colorectal cancer cell lines. Total protein extracts were collected from cells of the colorectal cancer cell lines DLD-1 and HCT-116 as well as from normal colonic epithelial cells (IECs) and evaluated for SMAD7 expression by Western blotting (FIG. 1C). IECs were isolated from the macroscopically and microscopically unaffected mucosa of patients undergoing colectomy for sporadic colorectal cancer. Western blotting revealed markedly higher expression of SMAD7 protein in DLD-1 and HCT-116 cells compared to IECs. Additionally, Western blot detection of SMAD7 protein in extracts collected from a series of colorectal cancer cell lines, including HCT-116, HT-115, HT-29, and DLD-1, revealed high levels of SMAD7 expression (FIG. 1D). In the same experiment, SMAD7 expression was evaluated in HepG2 cells, a hepatocellular carcinoma cell line known to express high levels of SMAD7 protein. β-actin was used as a loading control in both sets of experiments.

Figure 2:
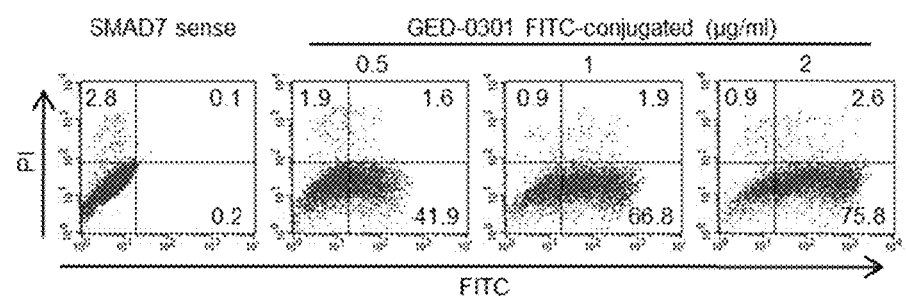
FIG. 2(A) is a series of dot-plots depicting the total number of cells and indicating percentages of propidium iodide (PI)- and fluorescent (FITC)-positive HCT-116 cells transfected with either unlabeled SMAD7 sense oligonucleotide or with increasing doses of the FITC-conjugated SMAD7 antisense oligonucleotide GED-0301 (GED-0301 FITC-conjugated)
FIG. 2(B) is a Western blot showing SMAD7 and β-actin levels in HCT-116 cells following transfection with either SMAD7 sense or GED-0301 oligonucleotides.
FIG. 2(C) depicts a graph showing the percent of proliferating HCT-116 or DLD-1 cells following no treatment (Untr) or transfection with SMAD7 sense or GED-0301 oligonucleotides (left) and histograms showing the percent of proliferating HCT-116 cells following transfection with SMAD7 sense (top) or GED-0301 (bottom) oligonucleotides.
FIG. 2(D) is a graph showing the percent of HCT-116 cells in different cell cycle phases following no treatment (Untr) or transfection with SMAD7 sense or GED-0301 oligonucleotides.
Figure 2:
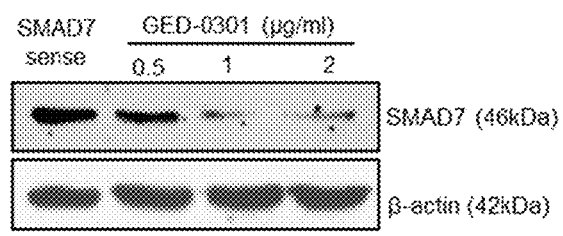
Figure 2:
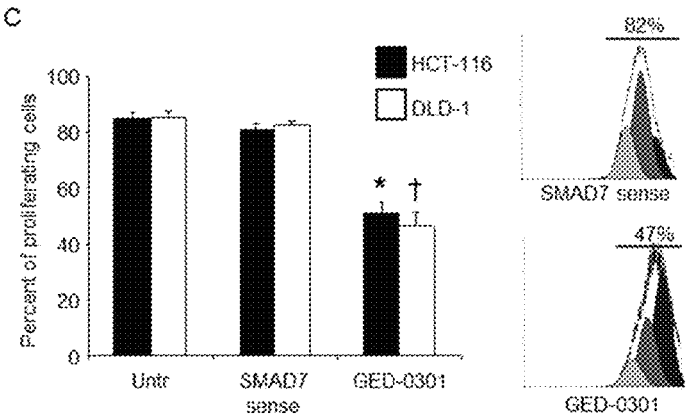
Figure 2:
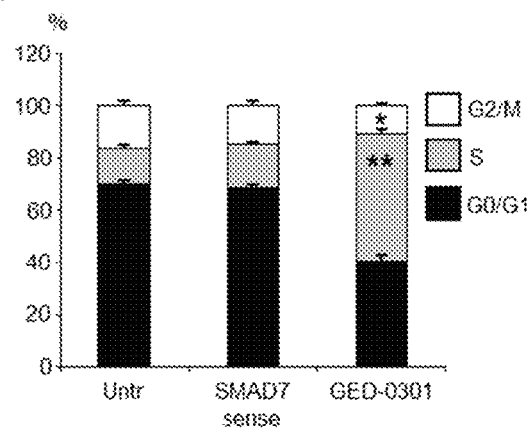

Example 2: Knockdown of Colorectal Cancer Cell SMAD7 Protein Levels by SMAD7 Antisense Oligonucleotide The transfection of cancer cells with the SMAD7 antisense oligonucleotide GED-0301 (SEQ ID NO: 6) was evaluated in cells of the HCT-116 cell line. HCT-116 cells were transfected with either unlabeled sense (SMAD7 sense) oligonucleotide or with increasing doses (0.5 μg/ml, 1 μg/ml, or 2 μg/ml) of FITC-conjugated GED-0301 for six hours. FIG. 2A shows representative dot-plots quantifying the percentages of PI-positive and FITC-positive transfected HCT-116 cells. High transfection efficiency was achieved with very low levels of cell death as evaluated by PI and FITC staining. One of two representative experiments in which similar results were obtained is shown in FIG. 2A.

Knockdown of SMAD7 protein levels following transfection of varying amounts of GED-0301 was also evaluated in HCT-116 cells. HCT-116 cells were transfected either with SMAD7 sense oligonucleotide (at 2 μg/ml) or GED-0301 (at 0.5 μg/ml, 1 μg/ml, or 2 μg/ml) for twelve hours. Cells were subsequently washed with phosphate buffered saline (PBS), cultured with fresh medium for six hours, washed again with PBS, and cultured for an additional 24 hours. SMAD7 and β-actin levels were then analyzed by Western blotting. FIG. 2B shows one of three representative experiments, demonstrating observable knockdown of SMAD7 protein levels in cells transfected with increasing amounts of GED-0301 as compared to cells transfected with SMAD7 sense oligonucleotide. These results demonstrated that a SMAD7 antisense oligonucleotide could be transfected into colorectal cancer cells and could induce robust knockdown of SMAD7 protein levels.

Example 3: SMAD7 Antisense Oligonucleotide Administration Affects Cell Cycle Dynamics in Colorectal Cancer Cells Cell proliferation was assessed in HCT-116 and DLD-1 cells following administration of SMAD7 sense and GED-0301 oligonucleotides. HCT-116 and DLD-1 cells were either not transfected (Untr) or transfected with SMAD7 sense or GED-0301 oligonucleotides at 1 μg/ml. Twelve hours post-transfection, cells were washed with PBS, cultured for six hours more, re-washed with PBS, and labeled with carboxyfluorescein diacetate succinimidyl ester (CFSE) for 30 minutes. Labeled cells were then washed with PBS and re-cultured in fresh medium for an additional 24 hours. The percentage of proliferating cells was evaluated by flow-cytometry. A significant decrease in cell proliferation was observed in both DLD-1 (white bars) and HCT-116 (black bars) cells transfected with GED-0301 as compared to cells transfected with SMAD7 sense oligonucleotide (FIG. 2C; HCT-116: SMAD7 sense-transfected cells vs GED-0301-transfected cells, *P<0.001; DLD-1: SMAD7 sense-transfected cells vs GED-0301-transfected cells, †P<0.001). Data in the graph depict the mean±standard deviation (SD) of three experiments. The histograms in FIG. 2C depict the total percent of cell proliferation in HCT-116 cells transfected with either SMAD7 sense (82%) or GED-0301 (47%) oligonucleotides from a single experiment. Thus, in the colorectal carcinoma cell lines HCT-116 and DLD-1 administration of a SMAD7 AS oligonucleotide resulted in a significant decrease in cell proliferation.

Distribution of cells in different cell cycle phases was also analyzed in HCT-116 cells following transfection of GED-0301. HCT-116 cells were either not transfected (Untr) or transfected with SMAD7 sense or GED-0301 oligonucleotides. HCT-116 cells were transfected with SMAD7 sense or GED-0301 oligonucleotides at 1 μg/ml. Twelve hours post-transfection, cells were washed with PBS and cultured in fresh medium for an additional 24 hours. The percentages of cells in different phases of the cell cycle was then assessed by flow cytometry. A statistically significant increase in the percentage of cells residing in S phase, and a statistically significant concomitant decrease in the percentage of cells constituting the G2/M population were observed in cells transfected with GED-0301 compared to controls (FIG. 2D; GED-0301-transfected cells vs SMAD7 sense-transfected cells, for S phase, *P=0.001; for G2/M phase, **P=0.01). One of three representative experiments in which similar results were obtained is shown. These results demonstrate that knockdown of SMAD7 protein facilitated by administration of the SMAD7 antisense oligonucleotide GED-0301 resulted in altered cell cycle phase population distribution in colorectal cancer cells.

Progression through the cell cycle is regulated by cyclin dependent kinases (CDKs), which associate with activating partners (i.e., cyclins) to regulate the activity of proteins that play roles in cell cycle progression. CDK activity is itself modulated by both inhibitory and activating phosphorylation. In particular, it is known that the CDK-cyclin complex can be inhibited by phosphorylation of Thr-14 and Tyr-15 residues within the ATP-binding pocket of the CDK. CDK2 plays a central role in the control of S-phase, binding to either cyclin E or cyclin A to regulate the G1/S transition and S phase progression, respectively.

Figure 3:
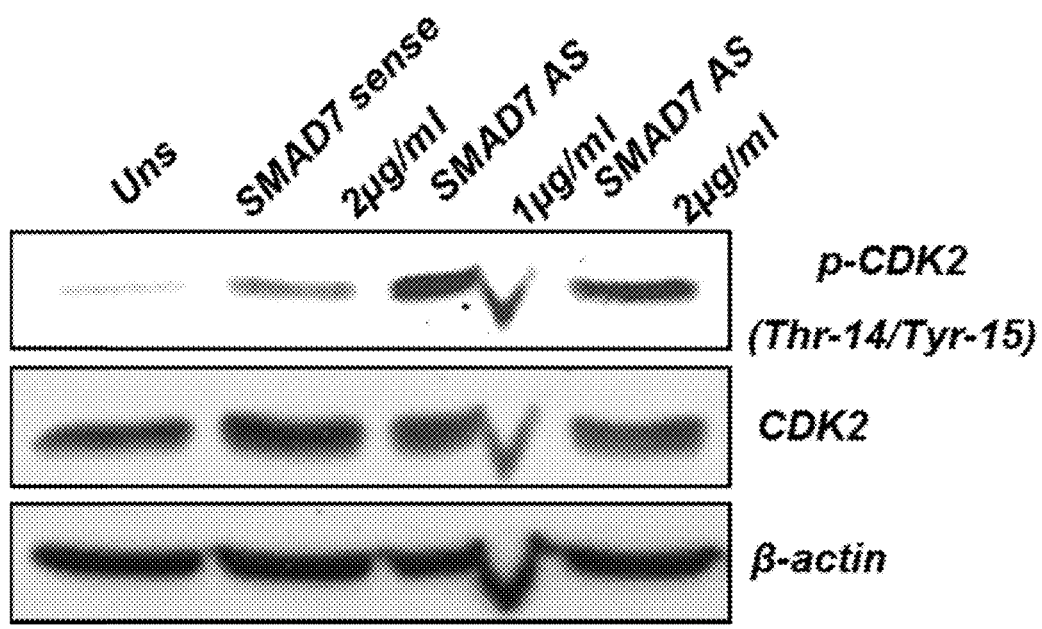
FIG. 3 is a Western blot showing expression levels in HCT-116 cells of CDK2 phosphorylated at Threoninine-14 or Tyrosine-15 (p-CDK2 (Thr-14/Tyr-15)), total CDK2 (CDK2), and β-actin following no stimulation (Uns) or transfection with SMAD7 sense or GED-0301 (SMAD7 AS) oligonucleotides.

The phosphorylation state of CDK2 was analyzed in HCT-116 following transfection with GED-0301. HCT-116 cells were either left unstimulated (Uns) or transfected with SMAD7 sense or SMAD7 AS oligonucleotide. HCT-116 cells were transfected with SMAD7 sense oligonucleotide at 2 μg/ml or SMAD7 AS oligonucleotide at 1 μg/ml or 2 μg/ml. Six hour post-transfection, cells were washed with PBS and re-cultured with fresh medium for an additional 16 hours. p-CDK2 (Thr-14/Tyr-15), CDK2, and β-actin levels were analyzed by Western blotting of cell extracts. One of three representative experiments in which similar results were obtained is shown in FIG. 3. The blot in FIG. 3 demonstrates that transfection of HCT-116 cells with GED-0301 resulted in a dramatic increase in p-CDK2 (Thr-14/Tyr-15) levels compared to controls, suggesting a mechanism to explain the accumulation of cells in S phase following GED-0301 administration.

Example 4: SMAD7 Antisense Oligonucleotide Administration Causes Increased Cell Death in Colorectal Cancer Cells Cell death was evaluated in HCT-116 cells following administration of the SMAD7 antisense oligonucleotide GED-0301 to determine whether the observed changes in cell cycle distribution correlated with activation of cell death programs. To investigate cell death, HCT-116 cells were either left untreated (Untr) or transfected with SMAD7 sense or GED-0301 oligonucleotide at 1 µg/ml for twelve hours. Cells were then washed with PBS, cultured for an additional six hours, re-washed with PBS, and cultured in fresh medium for another 24 (FIG. 4A, top panel) to 48 (FIG. 4A, middle panel) hours. Cell death was assessed by flow cytometry analysis of AV and/or PI staining. A significant increase in percent of cell death as assessed by the combined AV−/PI+, AV+/PI+, and AV+/PI− populations was observed at 48 hours for HCT-116 cells transfected with GED-0301 compared to cells transfected with SMAD7 sense oligonucleotide (FIG. 4A, middle panel; SMAD7 sense vs GED-0301, $P<0.001$). Results are expressed as the mean±SD of three experiments. Representative dot-plots (FIG. 4A, bottom panel) show the percentages of AV- and/or PI-positive HCT-116 cells 48 hours post-transfection.

Figure 4:
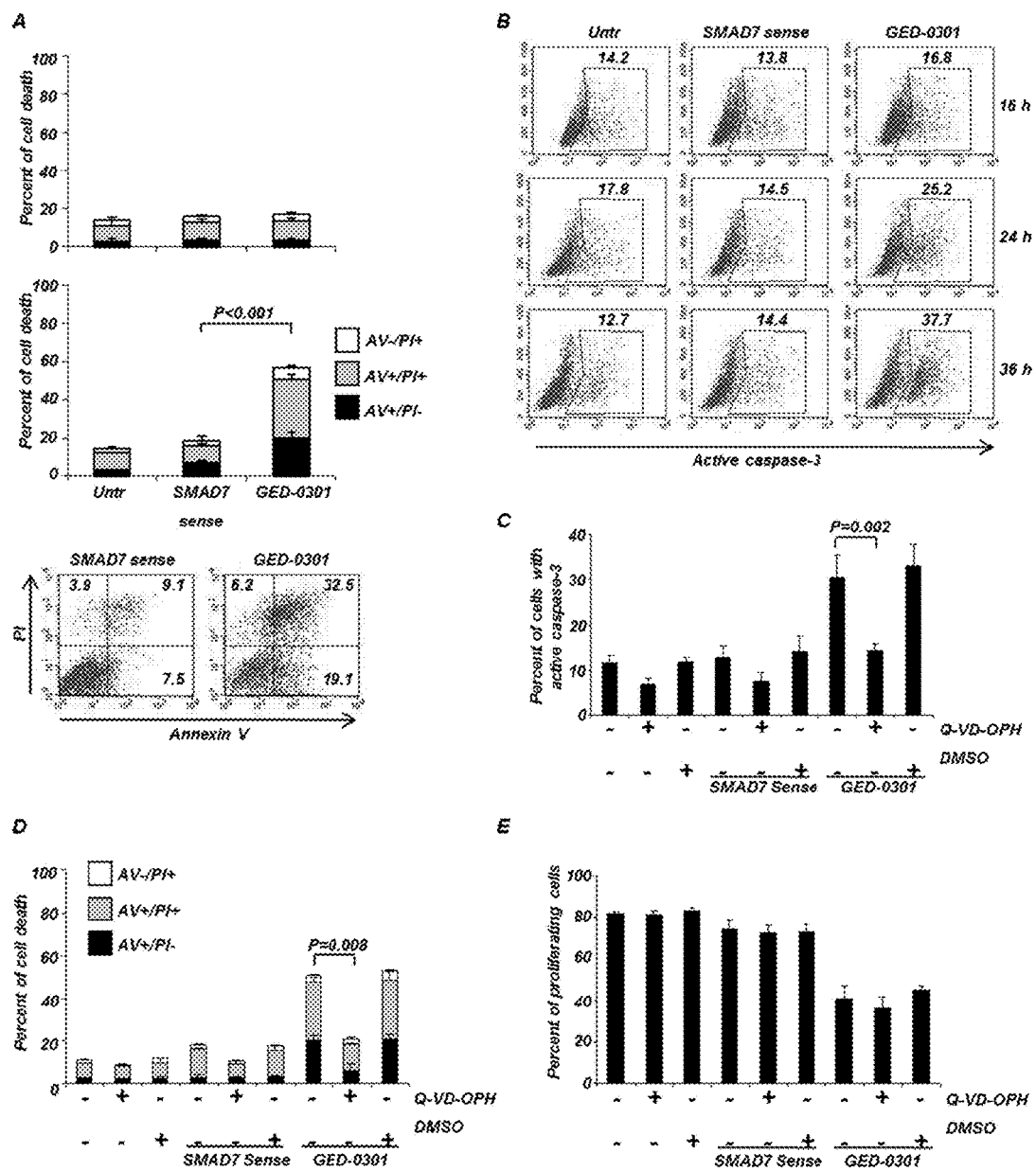
FIG. 4(A) shows graphs depicting the percent of HCT-116 cell death at 24 (top) or 48 hours (bottom) following no treatment (Untr) or transfection with either SMAD7 sense or GED-0301 oligonucleotides and dot-plots (bottom) illustrating PI and Annexin V (AV) staining following transfection of SMAD7 sense or GED-0301 oligonucleotides.
FIG. 4(B) shows a series of dot-plots quantifying active caspase-3 in HCT-116 cells at different time points following no treatment (Untr) or transfection of SMAD7 sense or GED-0301 oligonucleotides.
FIG. 4(C) is a graph showing the percent of cells exposed to N-(2-Quinolyl)valyl-aspartyl-(2,6-difluorophenoxy)methyl ketone (Q-VD-OPH) with active caspase-3 after no treatment or transfection with SMAD7 sense or GED-0301 oligonucleotides.
FIG. 4(D) is a graph showing the percent of cell death in cells exposed to Q-VD-OPH and then exposed to no treatment or transfection with SMAD7 sense or GED-0301 oligonucleotides.
FIG. 4(E) is a graph showing the percent of proliferating cells exposed to Q-VD-OPH followed by either no treatment or transfection with SMAD7 sense or GED-0301 oligonucleotides.

To further evaluate activation of cell death pathways in colorectal cancer cells following SMAD7 knockdown, the percent of cells expressing active caspase-3 was investigated in cells transfected with GED-0301. HCT-116 cells were either left untreated (Untr) or transfected with SMAD7 Sense or GED-0301 oligonucleotides at 1 µg/ml for twelve hours. Cells were then washed with PBS and cultured for another six hours with fresh complete medium before being washed with PBS and cultured in fresh medium for an additional 16, 24, or 36 hours. Activation of caspase-3 was then assessed by flow cytometry. The dot-plots in FIG. 4B show a notable increase in active caspase-3 in GED-0301-transfected cells compared to SMAD7 sense-transfected and untransfected cells. Moreover, GED-0301 transfection resulted in progressively higher percentages of active caspase-3 cells at each time point. These results demonstrate that in the HCT-116 colorectal cancer cell line, administration of GED-0301 resulted in a significant increase in the percent of cells undergoing cell death or expressing active caspase-3 compared to controls.

To determine whether cell death could be blocked in cells transfected with GED-0301, cells were cultured in normal media or in the presence of the pan-caspase inhibitor Q-VD-OPH or dimethyl sulfoxide (DMSO), for one hour, and then either left untreated or transfected with SMAD7 sense or GED-0301 oligonucleotides for 36 hours. The percent of cells expressing active capase-3 was assessed by flow cytometry. While no significant difference was observed in any of the untransfected or SMAD7 sense-transfected groups, a significant decrease in the percent of cells expressing active caspase-3 was observed between GED-0301-transfected cells exposed to no drug or exposed to Q-VD-OPH (FIG. 4C; No drug vs Q-VD-OPH, P=0.002).

The same protocol was used to assess the percent of cell death, except cells were assessed 48 hours post-transfection and percent of cell death was assessed by looking at the combined AV- and/or PI-positive populations within the total cell population. While no significant difference was observed in any of the untransfected or SMAD7 sense-transfected groups, a significant decrease in the percent of cells undergoing cell death was observed between GED-0301-transfected cells exposed to no drug or exposed to Q-VD-OPH (FIG. 4D; No drug vs Q-VD-OPH, P=0.008).

To determine whether GED-0301-induced HCT-116 cell growth arrest is secondary to induction of cell death, cell proliferation was assessed in GED-0301-transfected cells exposed to Q-VD-OPH. Cells were cultured in normal media or in the presence or absence of Q-VD-OPH or DMSO for one hour, and then either left untreated or transfected with SMAD7 sense oligonucleotide or GED-0301. After 24 hours the percentage of proliferating cells was assessed by flow cytometry. Regardless of Q-VD-OPH exposure, all GED-0301-transfected cell populations showed a decrease in percent of proliferating cells compared to the SMAD7 sense-transfected and untransfected groups, demonstrating that cell death is a secondary effect of decreased proliferation in colorectal cancer cells subjected to SMAD7 protein knockdown (FIG. 4E). Results shown in FIG. 4C-E are the mean±SD of three experiments.

Figure 5:
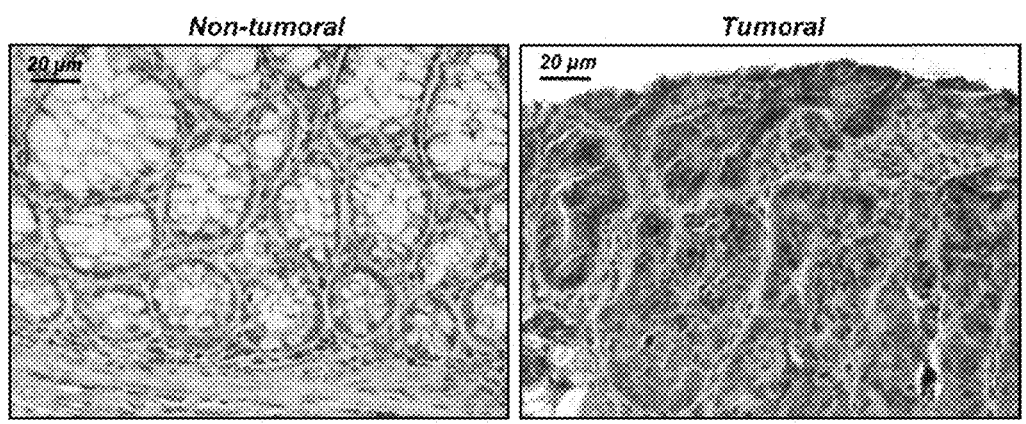
FIG. 5(A) shows SMAD7 immunostaining in non-tumoral or tumoral tissue from a mouse following azoxymethane and dextran sulfate sodium (AOM+DSS) treatment.
FIG. 5(B) is a graph showing relative SMAD7 mRNA expression in non-tumoral and tumoral tissue from mice following AOM+DSS treatment.
Figure 5:
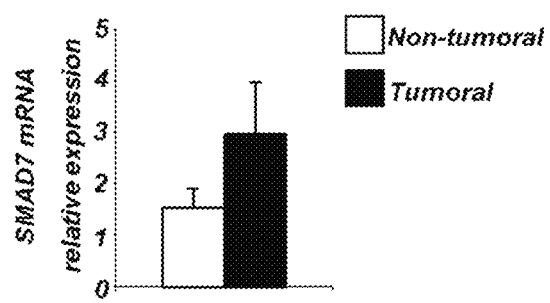

Example 5: In Vivo SMAD7 Protein and mRNA Expression are Increased in a Mouse Model of Colorectal Cancer SMAD7 protein and mRNA expression were evaluated in tumoral and non-tumoral areas of mice with colitis-associated colorectal cancer to determine whether induction of colorectal cancer in vivo was associated with increased SMAD7 levels. In the model utilized herein, C57BL/6J mice were administered AOM followed by repeated DSS ingestion (AOM+DSS), causing colonic inflammation and subsequent development of multiple colonic tumors. Animals were sacrificed 84 days after AOM+DSS treatment. SMAD7 protein levels were assessed by immunostaining of non-tumoral and tumoral areas of tissue collected from mice with colitis-associated colorectal cancer. FIG. 5A shows a clear increase in SMAD7 immunostaining in tumoral areas of AOM+DSS-treated mice. The image is taken from one of three experiments conducted. SMAD7 mRNA expression was also increased in tumoral areas compared to non-tumoral areas of AOM+DSS-treated mice as assessed by real-time PCR (FIG. 5B). Values in FIG. 5B represent the mean±SEM, and six mice were included in each group. Thus, increased SMAD7 mRNA and, in particular, protein expression in vivo was correlated with induction of colorectal cancer exclusively in tumoral tissue.

Figure 6:
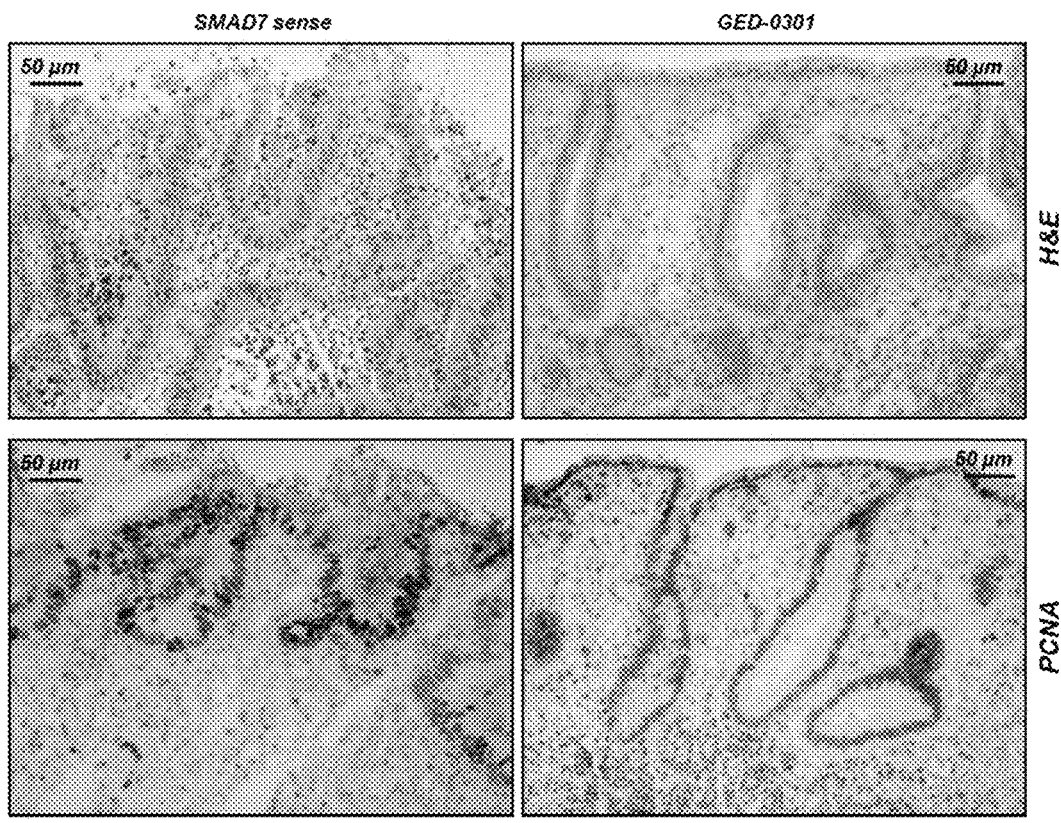
FIG. 6 shows hematoxylin and eosin (H&E) staining and Proliferating Cell Nuclear Antigen (PCNA) immunostaining of colorectal cancer tissue explants transfected with either SMAD7 sense or GED-0301 oligonucleotides.

Example 6: SMAD7 Antisense Oligonucleotide Administration Results in Decreased Tissue Explant Cell Proliferation To assess the effect of SMAD7 antisense oligonucleotide-facilitated knockdown on cell proliferation in tissue, H&E staining or PCNA immunostaining was performed on sections from ex-vivo colorectal cancer tissue explants. Fresh tissue explants were transfected with SMAD7 sense or GED-0301 oligonucleotides for 36 hours and then stained. FIG. 6 shows representative images of H&E- and PCNA-stained sections from freshly obtained explants. A clear decrease in both H&E staining and PCNA immunosignal was observed in tissue explants transfected with GED-0301 compared to explants transfected with SMAD7 sense oligonucleotide, demonstrating that GED-0301 efficiently reduced cell proliferation in transfected tissue. Images from one of two representative experiments is shown.

Figure 7:
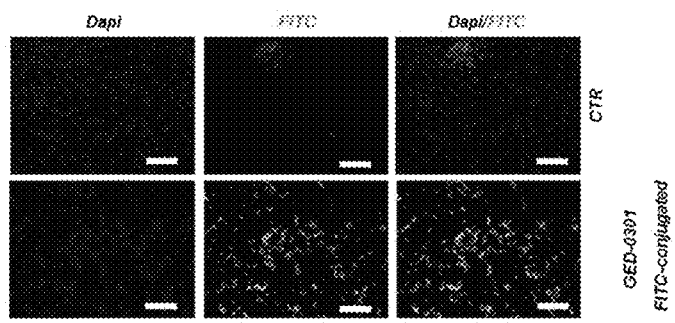
FIG. 7(A) shows distribution of FITC signal in HCT-116-derived xenografts exposed to a single injection of either PBS (CTR) or FITC-conjugated GED-0301 after injection into HCT-116-colonized Rag1$^{-/-}$ mice.
FIG. 7(B) is a Western blot showing SMAD7 and β-actin expression in protein extracts of HCT-116-derived xenografts exposed to either SMAD sense or GED-0301 oligonucleotides.
FIG. 7(C) is a graph quantifying tumor volume of xenografts derived from mice treated with either SMAD7 sense or GED-0301 oligonucleotides (left) and a representative photograph of xenografts from the same experiment.
FIG. 7(D) shows PCNA immunostaining of xenografts treated with either SMAD7 sense or GED-0301 oligonucleotides.
Figure 7:
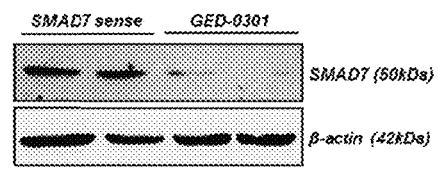
Figure 7:
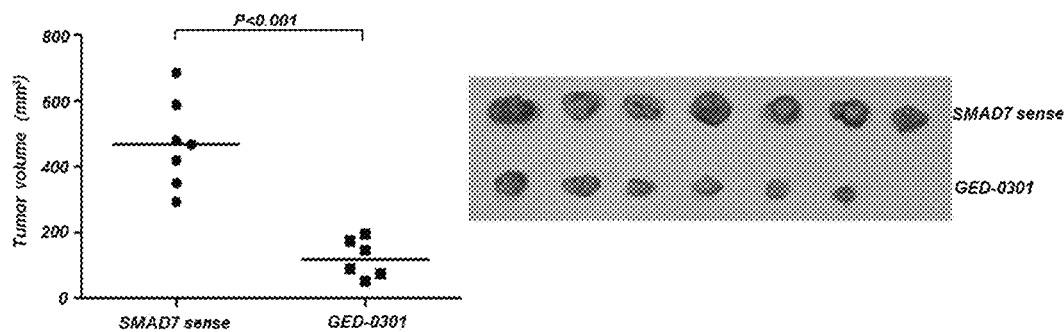
Figure 7:
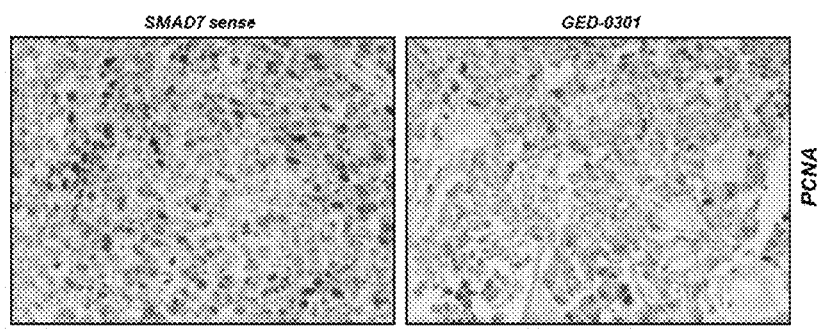

Example 7: SMAD7 Antisense Oligonucleotide Administration Reduces Colorectal Cancer Tumor Growth and Cell Proliferation In Vivo An HCT-116 xenograft model was used to assess the effect of GED-0301 administration upon colorectal cancer tumor development and colorectal cancer cell proliferation. To that end, Rag-1$^{-/-}$ mice were inoculated with HCT-116 cells. One week post-inoculation, mice received a single intraperitoneal injection of either PBS (FIG. 7A, CTR) or 100 µg of FITC-conjugated GED-0301 (FIG. 7A, GED-0301 FITC-conjugated). Mice were sacrificed 24 hours after reagent injection, tumors were excised, and FITC-conjugated GED-0301 distribution was assessed by immunofluorescent signal. FITC signal clearly co-localized with nuclear signal from xenograft cells (FIG. 7A, Dapi/FITC panel).

SMAD7 protein signal was also assessed in xenografts from animals subjected to GED-0301 administration. HCT-116 cells were inoculated into Rag-1$^{-/-}$ mice, and animals were treated intraperitoneally with either SMAD7 sense or GED-0301. Both oligonucleotides were administered at 100 µg/mouse every day, starting 7 days after HCT-116 injection. Mice were sacrificed 21 days after HCT-116 cell inoculation. Western blotting of total protein extract from xenograft tissue revealed observably decreased levels of SMAD7 signal in samples from GED-0301-treated mice but not SMAD7 sense-treated mice (FIG. 7B). β-actin was used as loading control. Thus, GED-0301 was able to knock down levels of SMAD7 protein in colorectal cancer xenograft cells in vivo.

Xenografts harvested in mice subjected to the same protocol described above were analyzed for the volume of tumors generated in each group. A significant decrease in tumor volume was observed in HCT-116-inoculated mice treated with GED-0301 compared to mice treated with SMAD7 sense oligonucleotide (FIG. 7C, SMAD7 sense vs GED-0301, $P<0.001$). Each point on the graph in FIG. 7C represents the volume of a single tumor. Horizontal bars indicate the median tumor volume in each group. One of two independent experiments in which similar results were obtained is shown. FIG. 7C provides a representative photograph of xenografts developed in SMAD7 sense-treated (top row) and GED-0301-treated (bottom row) mice.

Immunostaining for the cell proliferation marker PCNA was also performed in xenograft tissue sections harvested from mice that underwent the same protocol described above. Representative images of PCNA-stained xenograft sections are shown in FIG. 7D. A decrease in PCNA signal was observed in tissue sections taken from xenografts developed in GED-0301-treated mice as compared to those from SMAD7 sense-treated mice, demonstrating that SMAD7 antisense oligonucleotide-mediated knockdown of SMAD7 protein resulted in decreased cell proliferation in colorectal cancer cells in vivo. One of 3 representative experiments is shown.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A method of treating sporadic colorectal cancer in a patient suffering from sporadic colorectal cancer, the method comprising administering an effective amount of a SMAD7 antisense oligonucleotide comprising the nucleotide sequence of SEQ ID NO: 10 to the patient.

2. The method of claim 1, wherein all of the internucleoside bonds of the nucleotide sequence of SEQ ID NO: 10 are phosphorothioate bonds.

3. The method claim 1, wherein the SMAD7 antisense oligonucleotide is administered parenterally.

4. The method of claim 1, wherein the SMAD7 antisense oligonucleotide is administered orally.

5. A method of treating sporadic colorectal cancer or inhibiting the growth of sporadic colorectal cancer cells in a patient suffering from sporadic colorectal cancer, the method comprising administering to the patient an effective amount of a SMAD7 antisense oligonucleotide comprising the nucleotide sequence of SEQ ID NO: 10.

6. The method of claim 5, wherein all of the internucleoside bonds of the nucleotide sequence of SEQ ID NO: 10 are phosphorothioate bonds.

7. The method of claim 5, wherein said administering comprises administering a pharmaceutical composition comprising the SMAD7 antisense oligonucleotide and a pharmaceutically acceptable carrier.

8. The method of claim 7, wherein the pharmaceutical composition is administered parenterally.

9. The method of claim 7, wherein the pharmaceutical composition is administered orally.

10. The method of claim 9, wherein the pharmaceutical composition comprises an enteric coating comprising an ethylacrylate-methacrylic acid copolymer.

11. The method of claim 1 or 7, comprising administering at least 100 µg of the SMAD7 antisense oligonucleotide.

12. The method of claim 11, comprising administering from 35 mg to 500 mg of the SMAD7 antisense oligonucleotide.

13. The method of claim 1 or 5, wherein the patient is a human.

* * * * *

SEQUENCE LISTING

```
<160> NUMBER OF SEQ ID NOS: 12

<210> SEQ ID NO 1

<400> SEQUENCE: 1

000

<210> SEQ ID NO 2

<400> SEQUENCE: 2

000

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtcgcccctt ctccccgcag c                                                   21

<210> SEQ ID NO 4
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Cytosine, 5-methylcytosine or a
      2'-O-methylcytosine nucleoside
<220> FEATURE:
<221> NAME/KEY: modified_base
<222> LOCATION: (4)..(4)
<223> OTHER INFORMATION: Guanine, 5-methylguanine or a
      2'-O-methylguanine nucleoside
<220> FEATURE:
<221> NAME/KEY: modified_base
<222> LOCATION: (16)..(16)
<223> OTHER INFORMATION: Cytosine, 5-methylcytosine or a
      2'-O-methylcytosine nucleoside
<220> FEATURE:
<221> NAME/KEY: modified_base
<222> LOCATION: (17)..(17)
<223> OTHER INFORMATION: Guanine, 5-methylguanine or a
      2'-O-methylguanine nucleoside

<400> SEQUENCE: 4
gtcgcccctt ctccccgcag                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate

<400> SEQUENCE: 5
gtcgcccctt ctccccgcag                                              20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate

<400> SEQUENCE: 6
gtcgcccctt ctccccgcag c                                            21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 7
gtcgcccctt ctccccgcag                                                  20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 8
gtcgcccctt ctccccgcag c                                                21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl 2'-deoxycytidine
      5'-monophosphorothioate
<220> FEATURE:
<221> NAME/KEY: modified_base
<222> LOCATION: (16)..(16)
<223> OTHER INFORMATION: 5-methyl 2'-deoxycytidine
      5'-monophosphorothioate

<400> SEQUENCE: 9
gtcgcccctt ctccccgcag                                                  20

<210> SEQ ID NO 10
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl 2'-deoxycytidine
      5'-monophosphorothioate
<220> FEATURE:
<221> NAME/KEY: modified_base
<222> LOCATION: (16)..(16)
<223> OTHER INFORMATION: 5-methyl 2'-deoxycytidine
      5'-monophosphorothioate

<400> SEQUENCE: 10 gtcgccccctt ctccccgcag c                                              21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylthiophosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylthiophosphonate

<400> SEQUENCE: 11 gtcgccccctt ctccccgcag                                                20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylthiophosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylthiophosphonate

<400> SEQUENCE: 12 gtcgccccctt ctccccgcag c                                              21
```